US006898595B2

(12) United States Patent
Vivier et al.

(10) Patent No.: US 6,898,595 B2
(45) Date of Patent: May 24, 2005

(54) SEARCHING AND MATCHING A SET OF QUERY STRINGS USED FOR ACCESSING INFORMATION IN A DATABASE DIRECTORY

(75) Inventors: Barbara Jean Vivier, Niskayuna, NY (US); Kareem Sherif Aggour, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 422 days.

(21) Appl. No.: 10/094,894

(22) Filed: Mar. 12, 2002

(65) Prior Publication Data

US 2002/0120623 A1 Aug. 29, 2002

Related U.S. Application Data

(63) Continuation-in-part of application No. 09/760,995, filed on Jan. 16, 2001.
(60) Provisional application No. 60/241,645, filed on Oct. 19, 2000.

(51) Int. Cl.$^7$ .............................................. G06F 17/30
(52) U.S. Cl. ......................................................... 707/6
(58) Field of Search ........................................ 707/6, 2

(56) References Cited

U.S. PATENT DOCUMENTS

| | | | |
|---|---|---|---|
| 5,941,947 A | | 8/1999 | Brown et al. |
| 6,067,548 A | | 5/2000 | Cheng |
| 6,233,586 B1 | * | 5/2001 | Chang et al. ........... 707/103 R |
| 6,311,194 B1 | * | 10/2001 | Sheth et al. ................ 715/505 |
| 6,345,266 B1 | * | 2/2002 | Ganguly et al. ............... 707/1 |
| 6,426,955 B1 | * | 7/2002 | Gossett Dalton et al. ... 370/401 |
| 6,513,036 B2 | * | 1/2003 | Fruensgaard et al. .......... 707/4 |
| 6,539,382 B1 | * | 3/2003 | Byrne et al. .................. 707/10 |
| 6,560,595 B1 | * | 5/2003 | Sanders et al. ................ 707/2 |

OTHER PUBLICATIONS

Oblix NetPoint 4.0 [online]. Oblix, Inc. [retrieved on Dec. 18, 2000]. Retrieved from the Internet:<URL:http://www.oblix.com/products_and_solutions/netpoint/>.
Securant Products [online]. Securant Technologies [retrieved on Dec. 18, 2000]. Retrieved from the Internet: <URL: http://www.securant.com/ie/main_products.html>.
Delegated Management Services [online]. Netegrity, Inc. [retrieved on Dec. 18, 2000]. Retrieved from the Internet: <URL: http://www.netegrity.com/products/dms.html>.
Iplanet Delegated Administrator 4.5 Datasheet [online]. iPlanet International [retrieved on Dec. 18, 2000]. Retrieved from the Internet:<URL: http://iplanet.com/products/infrastructure/dir_security/del_admin/>.

* cited by examiner

*Primary Examiner*—Wayne Amsbury
(74) *Attorney, Agent, or Firm*—Fletcher Yoder

(57) ABSTRACT

Searching and matching a set of query strings used for accessing information in a database directory. In this disclosure, a user community administration tool queries a database directory containing user information associated with a user community. In the user community administration tool, there is an input query generation component that generates an input query having a search pattern that includes a combination of attribute names, logical, operators and attribute values. An accessing component accesses a library of queries used for accessing the user information in the database directory. A partitioning component partitions each of the queries in the library into logical units. Each logical unit comprises a combination of an attribute name, logical operator and attribute value. A comparing component compares the search pattern of the input query to each partitioned logical unit for each of the queries in the library. The comparing component compares the attribute name of the input query to the attribute name in the logical unit, the operator used in the input query to the operator used in the logical unit and the attribute value in the input query to the attribute value in the logical unit. A determining component determines whether there is a match between the input query and any of the logical units associated with each of the queries in the library.

29 Claims, 16 Drawing Sheets

Domain Tree Browser Search

To view the administrators of a domain, first select a configuration. Once a configuration has been selected, you may then enter a search criterion for finding domains within the configuration. After submitting a search criterion, a list of those domains satisfying the criterion will be shown. If any domains are returned, the domain name will be click-able to take you to a page showing the administrators for that domain as well as those of the domain's ancestors and descendants.

Select a Configuration

[ Demo Configuration ]

Enter Domain Search Criterion

[ Applications ] [ = ] [          ]

Copyright 2000-2001 General Electric Company

*Fig. 12d*

Domain Tree Browser Search

To view the administrators of a domain, first select a configuration. Once a configuration has been selected, you may then enter a search criterion for finding domains within the configuration. After submitting a search criterion, a list of those domains satisfying the criterion will be shown. If any domains are returned, the domain name will be click-able to take you to a page showing the administrators for that domain as well as those of the domain's ancestors and descendants.

Select a Configuration

Demo Configuration

Enter Domain Search Criterion

Email | "nb*"

Exactly Matching Domains

| Domain | Query Rule |
|---|---|
| GEMS | (!(gessocompanyname=GE Medical Services)(mail=*med.ge.com)) |
| NBC | (!(gessocompanyname=NBC)(mail=*@nbc.com)) |

*Fig. 12e*

SEARCHING AND MATCHING A SET OF QUERY STRINGS USED FOR ACCESSING INFORMATION IN A DATABASE DIRECTORY

CROSS REFERENCE TO RELATED APPLICATIONS

This application is a continuation-in-part of U.S. patent application Ser. No. 09/760,995, entitled "Delegated Administration Of Information In A Database Directory Using At Least One Arbitrary Group Of Users", filed Jan. 16, 2001, which claims the benefit of U.S. Provisional Application Ser. No. 60/241,645 filed on Oct. 19, 2000, entitled "Approach And Design For Software To Facilitate Delegated Administration Of Information In A Database Directory".

BACKGROUND OF THE INVENTION

This disclosure relates generally to accessing information in a database directory and more particularly to querying a database directory containing user information associated with a user community.

Generally, a community is a group of people who typically share a common interest. With the advent of the Internet and e-commerce, many companies are forming communities through intranets and extranets, for employees, suppliers, partners and clients. The communities make it easier and less expensive for the employees, suppliers, partners and clients to work together. In the context of computer services, these people are known as computer users or simply users. Information on each of the users in the communities is stored in a broad range of directories and databases. The information may comprise the user's name, location, telephone number, organization, login identification, password, etc. Other information may comprise the user's access privileges to resources such as applications and content. The directories may also store information on the physical devices (e.g., personal computers, servers, printers, routers, communication servers, etc.) in the networks that support the communities. Additional information may comprise the services (e.g., operating systems, applications, shared-file systems, print queues, etc.) available to each of the physical devices. All of the above information is generally known as community-based computer services.

The administration (i.e., the creation, maintenance, modification, updating and disabling) of these community-based computer services becomes difficult as the communities grow in size and complexity. In many cases, administration becomes an almost impossible task, unless a community is subdivided into more manageable sub-communities. With the creation of these sub-communities, it becomes desirable to use a team of administrators who share responsibilities for administrating the community by assigning different individuals to administer the sub-communities. This type of administration is referred to as delegated administration.

Currently available administration tools that facilitate delegated administration do have their drawbacks. For instance, as the number of sub-communities grows, it becomes necessary to search through sub-community specifications to find any sub-community that satisfies a search pattern. There are several reasons why it may be necessary to search through sub-community specifications. One reason is to identify in which sub-communities a potential user would be a member. Another reason is to determine if a sub-community exists covering a subset of users with certain common characteristics. In effect, this type of search is analogous to finding all users with certain characteristics; however, the community search finds all communities with certain characteristics. The currently available administration tools do not have the functionality to search through sub-community specifications to find any sub-community that satisfies a search pattern. Therefore, there is a need for an administration tool that provides the capability to search through sub-community specifications to find any sub-community that satisfies a search pattern.

BRIEF SUMMARY OF THE INVENTION

In one embodiment of this disclosure, there is a method, tool and computer readable medium that stores instructions for instructing a computer system, to match an input query having a search pattern that includes a combination of attribute names, logical operators and attribute values to a library of queries used for accessing information in a database directory. In this embodiment, each of the queries in the library is partitioned into logical units. Each logical unit comprises a combination of an attribute name, logical operator and attribute value. For each of the queries in the library, the search pattern of the input query is compared to each partitioned logical unit. The comparing comprises comparing the attribute name of the input query to the attribute name in the logical unit, the operator used in the input query to the operator used in the logical unit and the attribute value in the input query to the attribute value in the logical unit. A determination of whether there is a match between the input query and any of the logical units associated with each of the queries in the library is made.

In a second embodiment of this disclosure, there is a method and computer readable medium that stores instructions for instructing a computer system, to match an input query having a search pattern that includes a combination of attribute names, logical operators and attribute values to a library of queries used for accessing information in a database directory. In this embodiment, each of the queries in the library is partitioned into logical units. Each logical unit comprises a combination of an attribute name, logical operator and attribute value. For each of the queries in the library, the search pattern of the input query is compared to each partitioned logical unit. The comparing comprises comparing the attribute name of the input query to the attribute name in the logical unit, the operator used in the input query to the operator used in the logical unit and the attribute value in the input query to the attribute value in the logical unit. A determination of whether there is a match between the input query and any of the logical units associated with each of the queries in the library is made. A match comprises an exact match and a near match.

In a third embodiment of this disclosure, there is a method and computer readable medium that stores instructions for instructing a computer system, to query a database directory containing user information associated with a user community. In this embodiment, an input query is generated having a search pattern that includes a combination of attribute names, logical operators and attribute values. A library of queries used for accessing the user information in the database directory is then accessed. Each of the queries in the library is partitioned into logical units. Each logical unit comprises an attribute name, logical operator and attribute value. For each of the queries in the library, the search pattern of the input query is compared to each partitioned logical unit. The comparing comprises comparing the attribute name of the input query to the attribute name in the logical unit, the operator used in the input query to the operator used in the logical unit and the attribute value in the input query to the attribute value in the logical unit. A determination of whether there is a match between the input query and any of the logical units associated with each of the queries in the library is made.

In another embodiment, there is a method and computer readable medium that stores instructions for instructing a computer system, to enable an administrator to query a database directory containing user information associated with a user community. In this embodiment, the administrator is prompted to generate an input query having a search pattern that includes a combination of attribute names, logical operators and attribute values. A library of queries used for accessing the user information in the database directory is accessed in response to the input query generated by the administrator. Each of the queries in the library is partitioned into logical units. Each logical unit comprises a combination of an attribute name, logical operator and attribute value. For each of the queries in the library, the search pattern of the input query is compared to each partitioned logical unit. The comparing comprises comparing the attribute name of the input query to the attribute name in the logical unit, the operator used in the input query to the operator used in the logical unit and the attribute value in the input query to the attribute value in the logical unit. A determination of whether there is a match between the input query and any of the logical units associated with each of the queries in the library is made. The administrator is informed of whether there is a match with the input query.

In a fifth embodiment, there is a user community administration tool for querying a database directory containing user information associated with a user community. In the user community administration tool there is an input query generation component that generates an input query having a search pattern that includes a combination of attribute names, logical operators and attribute values. An accessing component accesses a library of queries used for accessing the user information in the database directory. A partitioning component partitions each of the queries in the library into logical units. Each logical unit comprises a combination of an attribute name, logical operator and attribute value. A comparing component compares the search pattern of the input query to each partitioned logical unit for each of the queries in the library. The comparing component compares the attribute name of the input query to the attribute name in the logical unit, the operator used in the input query to the operator used in the logical unit and the attribute value in the input query to the attribute value in the logical unit. A determining component determines whether there is a match between the input query and any of the logical units associated with each of the queries in the library.

In still another embodiment, there is a system for querying user information associated with a user community. This system comprises a database directory that contains a plurality of user information. A user community administration tool queries the database directory. The user community administration tool comprises an input query generation component that generates an input query having a search pattern that includes a combination of attribute names, logical operators and attribute values. An accessing component accesses a library of queries used for accessing the user information in the database directory. A partitioning component partitions each of the queries in the library into logical units. Each logical unit comprises a combination of an attribute name, logical operator and attribute value. A comparing component compares the search pattern of the input query to each partitioned logical unit for each of the queries in the library. The comparing component compares the attribute name of the input query to the attribute name in the logical unit, the operator used in the input query to the operator used in the logical unit and the attribute value in the input query to the attribute value in the logical unit. A determining component determines whether there is a match between the input query and any of the logical units associated with each of the queries in the library. A computing unit is configured to serve the user community administration tool and the database directory.

BRIEF DESCRIPTION OF THE DRAWINGS

FIGS. 12a–12e show various screen displays that may be presented to a user of the delegated administration tool shown in FIG. 5.

DETAILED DESCRIPTION OF THE INVENTION

Figure 1:
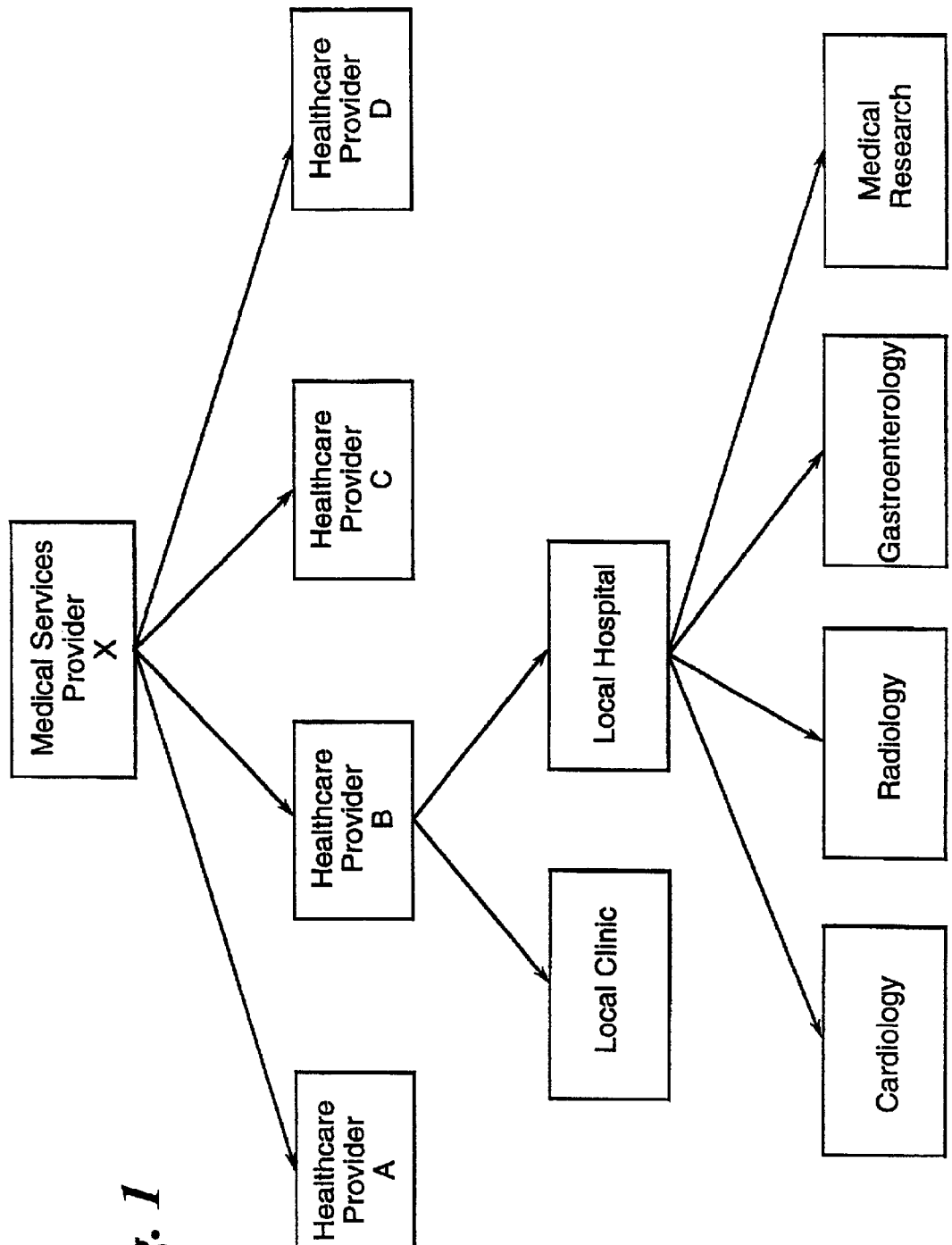
FIG. 1 shows a schematic of an example of a user community.

FIG. 1 shows a schematic of an example of a user community receiving a community of services from a medical services provider. The example shown in FIG. 1 is illustrative of the concept of a user community and is not meant to limit this disclosure. In FIG. 1, Healthcare Providers A–D are communities that receive computer-based services from Medical Services Provider X. Examples of such computer-based services may comprise medical information, the ability to order medical supplies, the ability to schedule patient appointments, the ability to file claims for patient services. Other illustrative examples of computer-based services for this scenario may comprise benchmarking information, healthcare statistics and access to downloadable software. The healthcare providers may also want to provide the computer-based services to their clients, partners, vendors, suppliers, etc. In FIG. 1, Healthcare Provider B provides the computer-based services established from Medical Services Provider X to a Local Clinic and Local Hospital with which it has a relationship. The computer-based services can also be provided to their employees. In FIG. 1, the computer-based services are provided to the various departments in the Local Hospital such as Cardiology, Radiology, Gastroenterology, Medical Research, etc. Similar types of distribution of the computer-based services can be provided for the other healthcare providers (i.e., Healthcare Providers A, C and D).

Medical Services Provider X stores information on each of the users in the community in a database directory. The information may comprise the user's name, location, telephone number, organization, login identification, password, etc. Other information may comprise the user's access privileges to certain resources provided by Medical Services Provider X such as applications and content. The database directory of Medical Services Provider may also store information on the physical devices (e.g., personal computers, servers, printers, routers, communication servers, etc.) in the networks that support the communities. Additional information stored in the database directory may comprise the services (e.g., operating systems, applications, shared-file systems, print queues, etc.) available to each of the physical devices.

Figure 2:
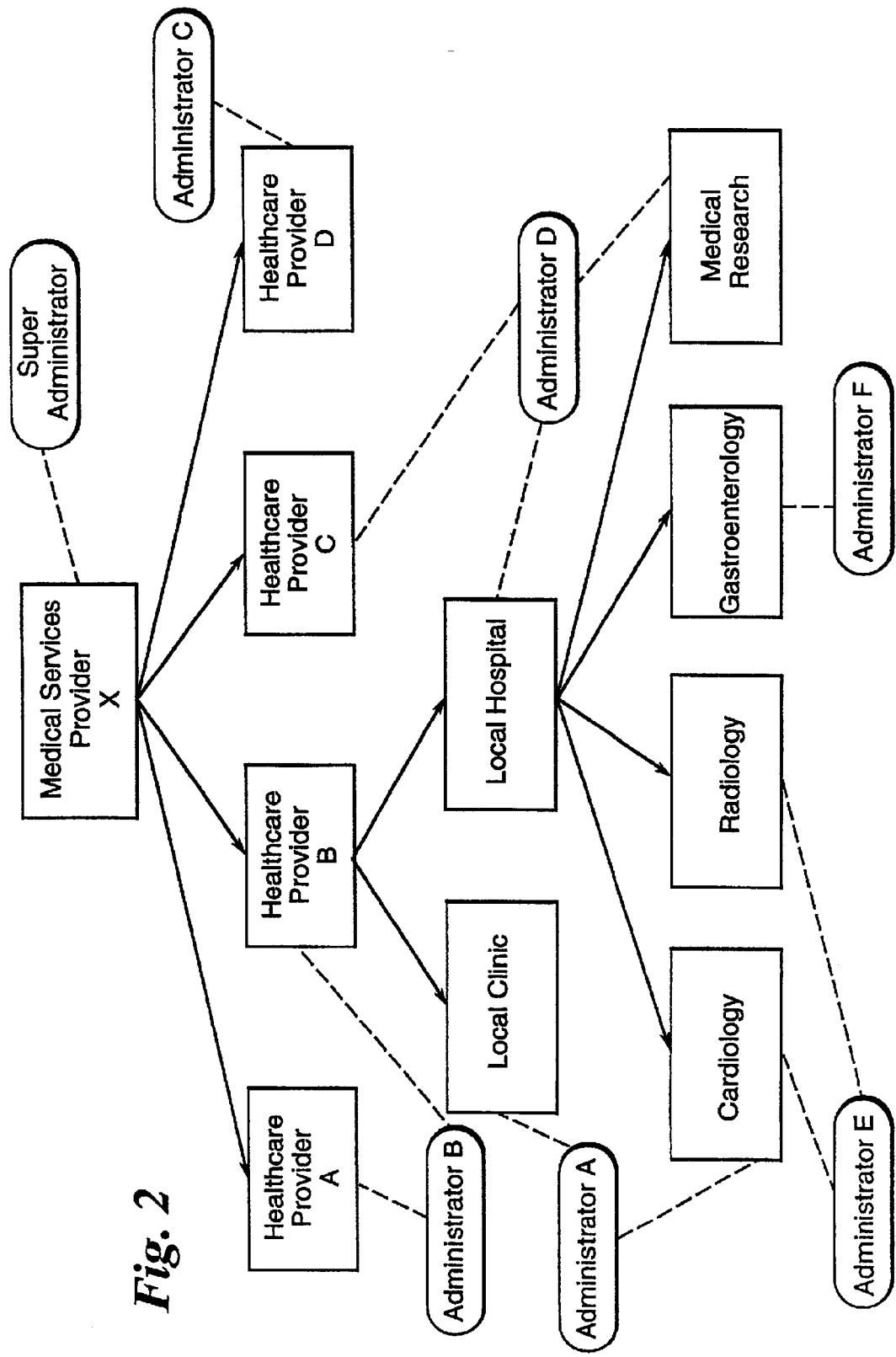
FIG. 2 shows an example of delegated administration of the user community shown in FIG. 1.

Since the user community shown in FIG. 1 can be quite large and complex, it is desirable to subdivide and delegate administration of these communities. FIG. 2 shows an example of delegated administration of the user community shown in FIG. 1. In this example, for each community there is an administrator that is responsible for managing a variety of activities that include but are not limited to modifying user information, updating permissions to certain resources, disabling user accounts, creating user accounts and maintaining user accounts. For instance, the SuperAdministrator manages the activities for Medical Services Provider X; Administrator A manages the activities for the Local Clinic associated with Healthcare Provider B and the Cardiology department of the Local Hospital; Administrator B manages the activities for Healthcare Providers A and B; Administrator C manages the activities for Healthcare Provider D; Administrator D manages the activities for the Local Hospital associated with Healthcare Provider B, the Medical Research departments for the Local Hospital associated with Healthcare Provider B, as well as the activities for Healthcare Provider C; Administrator E manages the activities for the Cardiology and Radiology departments of the Local Hospital associated with Healthcare Provider B: and Administrator F manages the activities for the Gastroenterology department of the Local Hospital associated with Healthcare Provider B. The extent to which Administrators A–F manage activities depends entirely on the type of authority that they have. Other forms of delegated administration for this example are possible as will be apparent to people skilled-in the art.

For purposes of explaining the delegated administration provided with this disclosure, each block (i.e., Medical Services Provider X, Healthcare Providers A–D, Local Clinic, Local Hospital, Cardiology, Radiology, Gastroenterology, Medical Research) in the user community of FIG. 2 represents an administrative domain. An administrative domain is a managed object that comprises a set of users, a set of user attributes which can be modified, and a set of allowable values for those data fields over which an administrator has authority. Possible examples of user attributes may include but are not limited to employer, role or job description, resources that permission has been granted to access, address and equipment used. Generally, an administrator's authority may comprise edit authority and/or delegation authority. An administrator has edit authority within the administrative domain when he or she may edit certain attributes of the users. An administrator has delegation authority within the administrative domain when he or she may define a subset of the users and identify attributes for modification, in order to create an administrative sub-domain. The assignment of the administrative sub-domain to a person is the delegation of that domain. The ability to create an administrative sub-domain and to assign that domain to a user is delegation authority. Although the authority described in this disclosure relates generally to edit authority and delegation authority, one of ordinary skill in the art will recognize that other types of authority such as view, modify, delete, temporary delegation as well as similar operations, but with limitations on the extent of viewable, modifiable data, etc., are possible as well. These examples of authority can be used in addition to, in place of, or in combination with the delegation and edit authority.

It is desirable to be able to create communities based on any user information without regard to structure or format of the underlying user data in the database directory. This would enable an administrator to administer user groups formed in many different and arbitrary sets, as opposed to groups that are formed from sets that are generally inflexible in definition (e.g., the strictly hierarchical organization model). For example, an administrator could administer any arbitrary grouping of users according to information such as the users' location, applications that users have access privileges to, contractual agreements that users have executed, etc.

Figure 3:
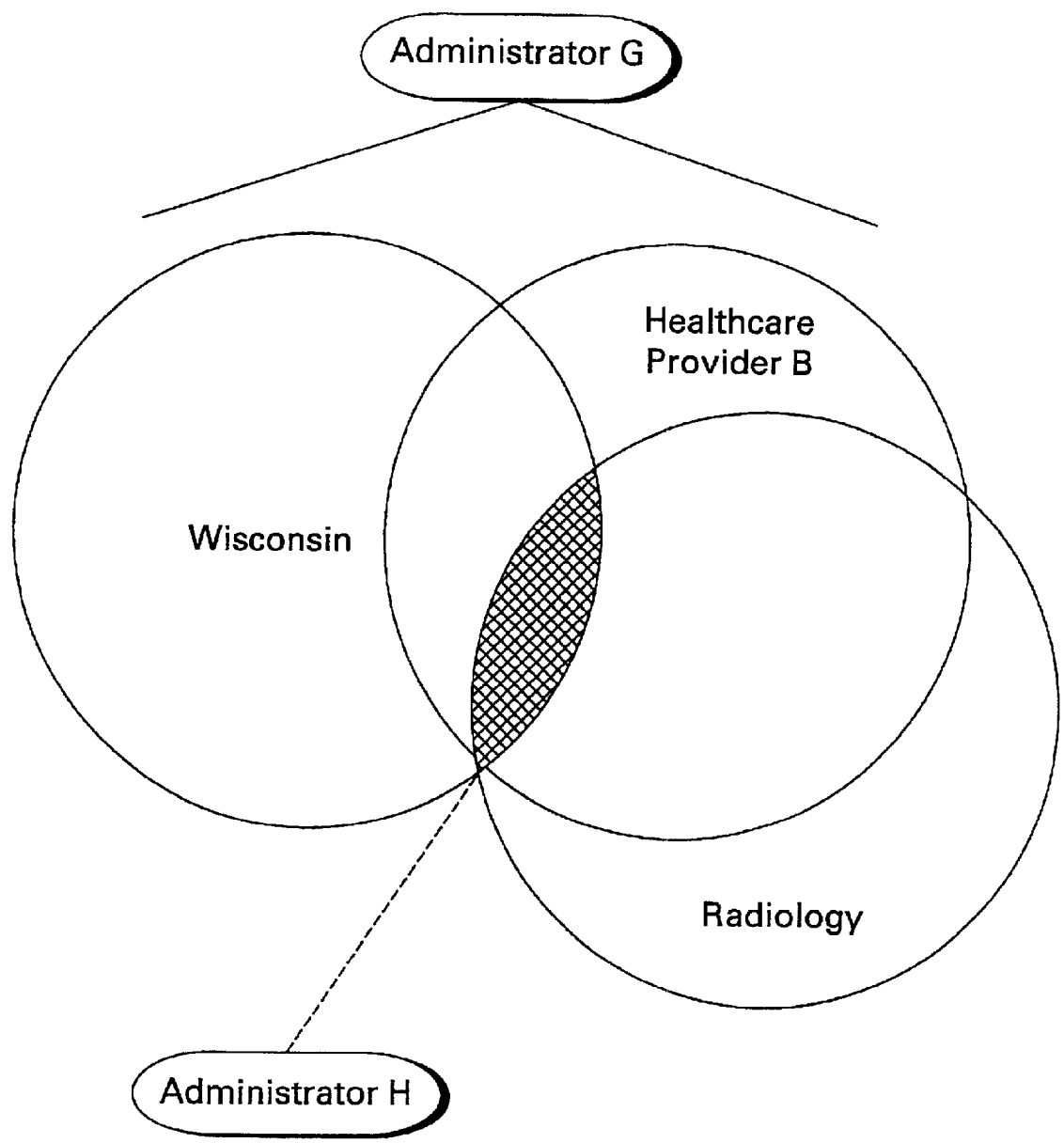
FIG. 3 shows an example of a user community formed from at least one arbitrary group of users.

FIG. 3 shows an example of a user community formed from at least one arbitrary group of users. In FIG. 3, the user community comprises Radiologists as one group, employees of Healthcare Provider B as a second group and employees located in the state of Wisconsin as a third group. Administrator G is the administrator assigned to the three user communities. Assuming that Administrator G has been granted at least delegation authority for at least one community (it is possible that other types of authority such as edit, view, modify, delete, etc. can be granted), then he or she can form an administrative domain from these groups of users. In FIG. 3, the administrative domain formed by Administrator G comprises Radiologists that work for Healthcare Provider B in the state of Wisconsin. A cross-hatched section in FIG. 3 represents the administrative domain of Radiologists that work for Healthcare Provider B in the state of Wisconsin. Assuming again that Administrator G has delegation authority, then he or she can grant administrative privileges for managing the administrative domain that comprises Radiologists that work for Healthcare Provider B in the state of Wisconsin. In FIG. 3, administrator G has assigned administrative privileges to Administrator H for the administrative domain that comprises of Radiologists that work for Healthcare Provider B in the state of Wisconsin. Assuming that Administrator H has been granted at least delegation authority for this domain from Administrator G, then it is also possible for Administrator H to create in administrative sub-domain from the domain of Radiologists that work for Healthcare Provider B in the state of Wisconsin by specifying an additional arbitrary user group from this domain. The specified additional arbitrary user group can be based upon whatever user attributes are desired without regard to structure or format of the underlying user data. For example, Administrator H could create a sub-domain for radiologists who are board certified, work in Madison, Wis., and work for Healthcare Provider B. Then Administrator H could grant administrative privileges to another administrator for this sub-domain if desired. The example shown in FIG. 3 is illustrative of the concept of creating a user community, administrative domain or sub-domain from at least one arbitrary group of users and is not meant to limit this disclosure.

Figure 4:
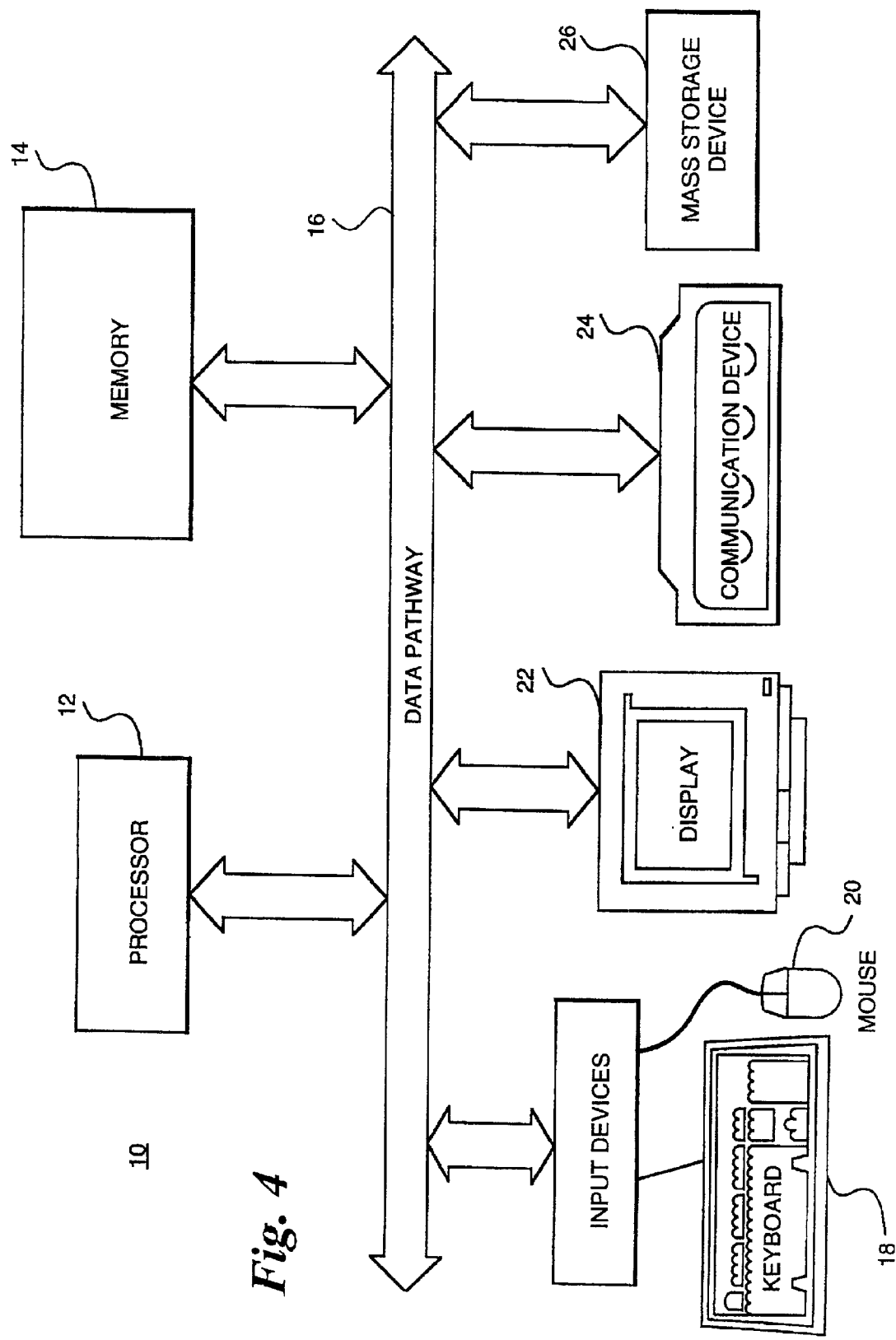
FIG. 4 shows a schematic of a general-purpose computer system in which a delegated administration tool that creates and administers at least one arbitrary group of users operates.

As an example, the above-described delegated administration capabilities for creating and administering at least one arbitrary group of users can be implemented in software. FIG. 4 shows a schematic of a general-purpose computer system 10 in which a delegated administration tool that creates and administers at least one arbitrary group of users operates. The computer system 10 generally comprises at least one processor 12, a memory 14, input/output devices, and data pathways (e.g., buses) 16 connecting the processor, memory and input/output devices. The processor 12 accepts instructions and data from the memory 14 and performs various calculations. The processor 12 includes an arithmetic logic unit (ALU) that performs arithmetic and logical operations and a control unit that extracts instructions from memory 14 and decodes and executes them, calling on the ALU when necessary. The memory 14 generally includes a random-access memory (RAM) and a read-only memory (ROM); however, there may be other types of memory such as programmable read-only memory (PROM), erasable programmable read-only memory (EPROM) and electrically erasable programmable read-only memory (EEPROM). Also, the memory 14 preferably contains an operating system, which executes on the processor 12. The operating system performs basic tasks that include recognizing input, sending output to output devices, keeping track of files and directories and controlling various peripheral devices.

The input/output devices may comprise a keyboard 18 and a mouse 20 that enter data and instructions into the computer system 10. Also, a display 22 may be used to allow a user to see what the computer has accomplished. Other output devices may include a printer, plotter, synthesizer and speakers. A communication device 24 such as a telephone or cable modem or a network card such as an Ethernet adapter, local area network (LAN) adapter, integrated services digital network (ISDN) adapter, or Digital Subscriber Line (DSL) adapter, that enables the computer system 10 to access other computers and resources on a network such as a LAN, a wide area network (WAN) or a wireless network. A mass storage device 26 may be used to allow the computer system 10 to permanently retain large amounts of data. The mass storage device may include all types of disk drives such as floppy disks, hard disks and optical disks, as well as tape drives that can read and write data onto a tape that could include digital audio tapes (DAT), digital linear tapes (DLT), or other magnetically coded media. The above-described computer system 10 can take the form of a hand-held digital computer, personal digital assistant computer, notebook computer, personal computer, workstation, mini-computer, mainframe computer or supercomputer.

Figure 5:
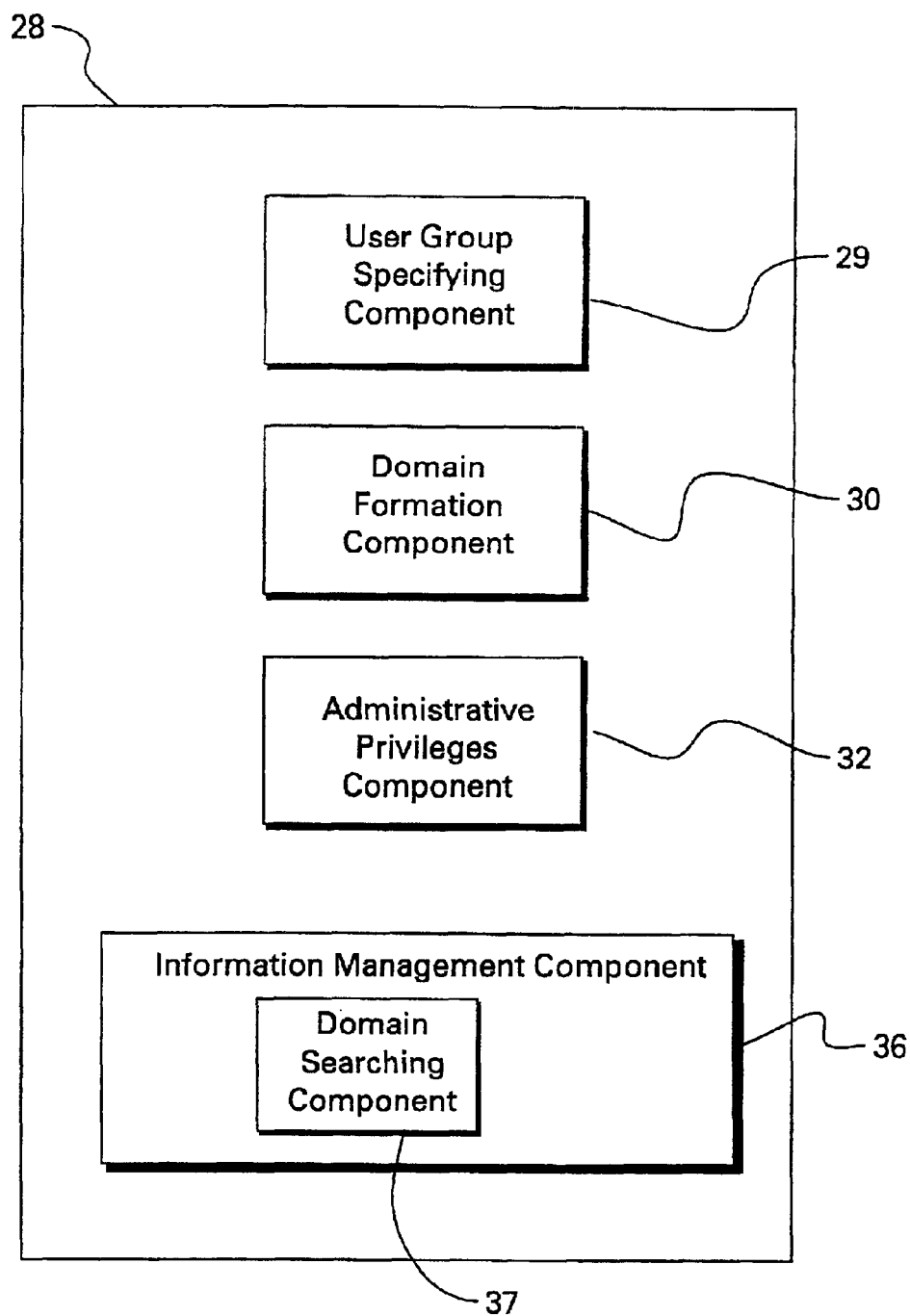
FIG. 5 shows a top-level component architecture diagram of the delegated administration tool that creates and administers at least one arbitrary group of users and that operates on the computer system shown in FIG. 4.

FIG. 5 shows a top-level component architecture diagram of a delegated administration tool 28 that can create and administer at least one arbitrary group of users and that operates on the computer system 10 shown in FIG. 4. The delegated administration tool 28 comprises a user group specifying component 29 that enables an administrator to specify at least one arbitrary group of users for a user community such as the one shown in FIG. 3. Each arbitrary group of users that is specified has attributes associated with each of its users and allowable values of these attributes. The administrator via the user group specifying component 29 uses combinations of possible attribute values for each of the users as criteria for specifying the at least one arbitrary group of users. The specified at least one arbitrary group of users can be based upon whatever user attributes are desired by the administrator without regard to structure or format of the underlying user data. For example, referring to FIG. 3, an administrator can use the user group specifying component 29 to utilize user attributes and values such as employer (Healthcare Provider B), job description (radiologist) and address (Wisconsin) to form a user community.

The user group specifying component 29 forms the at least one arbitrary group of users through a query rule constructed by the administrator to query a database directory containing user information. The query rule defines the users within the at least one arbitrary group of users. Since the database directory may not be organized according to the desired grouping of users because of variables such as cross-functionalities of users, different locations of users, etc., the query rule aids the administrator in specifying the at least one arbitrary group of users. The formation of the at least one arbitrary group of users is dynamic because user data in the database directory that satisfies the query rule dynamically becomes a managed user within the at least one arbitrary group of users in real-time. That is, the at least one arbitrary group of users is formed on demand by execution of the query. Thus, if any new user is added to the database directory and his or her data would result in satisfying the query rule, then that user dynamically becomes a managed user within the domain formed from the at least one arbitrary group of users in real-time. Alternatively, if a user is removed from the database directory, then that user is dynamically and in real-time excluded as a managed user for the domain formed from the at least one arbitrary group of users. Also, if the user data changes such that a user's new data no longer satisfies the query, then the user is dynamically and in real-time excluded as a managed user for the domain. The dynamic formation of the at least one arbitrary group of users enables an administrator to determine who is currently in the administrative domain formed from the at least one arbitrary user group and who is not.

A domain formation component 30 enables an administrator to form a user community, administrative domain or administrative sub-domain from the specified at least one arbitrary group of users such as the ones shown and described with FIG. 3. For example, referring to FIG. 3, the domain formation component 30 permits an administrator to form an administrative domain from the at least one arbitrary group of users that have user attributes and values for those who are employed by Healthcare Provider B, in the state of Wisconsin, as radiologists.

The delegated administration tool 28 also comprises an administrative privileges component 32. The administrative privileges component 32 enables an administrator to grant administrative privileges for an administrative domain or administrative sub-domain that he or she has authority for in accordance with the above-described manner. The granted administrative privileges may comprise at least one of delegation authority and edit authority. As mentioned above, it is also possible to grant other types of authority such as view, modify, delete, temporary delegation, etc. These examples of authority can be used in addition to, in place of, or in combination with the delegation and edit authority.

The administrative privileges component 32 also enables an administrator to define which users in an administrative domain or sub-domain that he or she operates and has authority for will have the granted administrative privileges. More specifically, an administrator can use this component to define various administrators for their operational domain by assigning delegation authority, edit authority or other types to a particular user. Administrators with delegation authority can also use the user group specifying component 29, domain formation component 30 and administrative privileges component 32 to form sub-domains from an additional group of users for their operational domain by constructing a query rule, defining administrative privileges for these newly formed sub-domains and defining who will have delegation authority, edit authority or other types for these sub-domains. As long as an administrator has delegation authority in a particular domain, it is possible to continue to use the user group specifying component 29, domain formation component 30 and administrative privileges component 32 to create a sub-domain from at least one arbitrary group of users using a query rule and delegate administration for the sub-domain that he or she operates in. For instance, using an earlier example, Administrator H could create a sub-domain for radiologists who are board certified, work in Madison, Wis., and work for Healthcare Provider B. Assuming that Administrator H has delegation authority, he or she can grant administrative privileges to other administrators, if desired, for this sub-domain. An administrator that is assigned delegation authority for this sub-domain can continue to create an additional sub-domain (e.g., board-certified radiologists working in Madison, Wis., for Healthcare Provider B, that are trained to use X-ray Scanner Z) of the current domain and grant authority for it to another administrator. It is possible to continue to an arbitrary level with respect to an administrator's working domain.

The delegated administration tool 28 also comprises an information management component 36 that manages information associated with each of the administrative domains in accordance with the delegated administrative privileges. Depending on the type of authority delegated, an administrator can use the information management component 36 to edit, view or delete specific attributes for a user in a domain. The information management component 36 is not limited to these functions and may perform other functions such as generating reports (e.g., reports on all users within a domain), analyzing data (e.g., determining how frequently some types of data change), performing statistical analysis or allowing users to perform self-administration on certain attributes (e.g., phone number, e-mail address, passwords, etc.).

FIG. 5 also shows that the information management component 36 comprises a domain searching component 37 that an administrator can use to query a database directory containing user information associated with the domains and sub-domains. As mentioned above, query rules are used to form the at least one arbitrary group of users. In this disclosure, the query rules are stored as a library apart from the database directory and are used to search and match domain and sub-domain specifications. One of ordinary skill in the art will recognize that other approaches can be used to store the query rules such as executable code fragments. The domain searching component 37 searches the library of queries and finds those queries that exactly match or nearly match a given search pattern associated with an input query. Each pattern supplies an attribute name, logical operators (e.g., =, <=, >=, ~=, etc.) and attribute values. For example, a possible pattern for an input query could be (title ~=*radiologist). In this example, title is the attribute name, ~= is the logical operator and *radiologist is the attribute value, where * is a wildcard character that stands for one or more arbitrary characters. An example of one query in the library of queries could be (&,(sn=*Neil)(title=radiologist)), which finds people with a surname that has Neil (e.g., O'Neil, McNeil, etc.) in it and that has a title of radiologist. These examples are for the purpose of understanding the concepts presented in this disclosure and one of ordinary skill in the art will recognize that the input query and queries in the library could be more complicated. Using these examples, the domain searching component 37 would determine that there is either an exact match or near match between the input query and the query in the library. Below is a more detailed discussion on how and why the domain searching component 37 would find an exact match or near match between the two.

Figure 6:
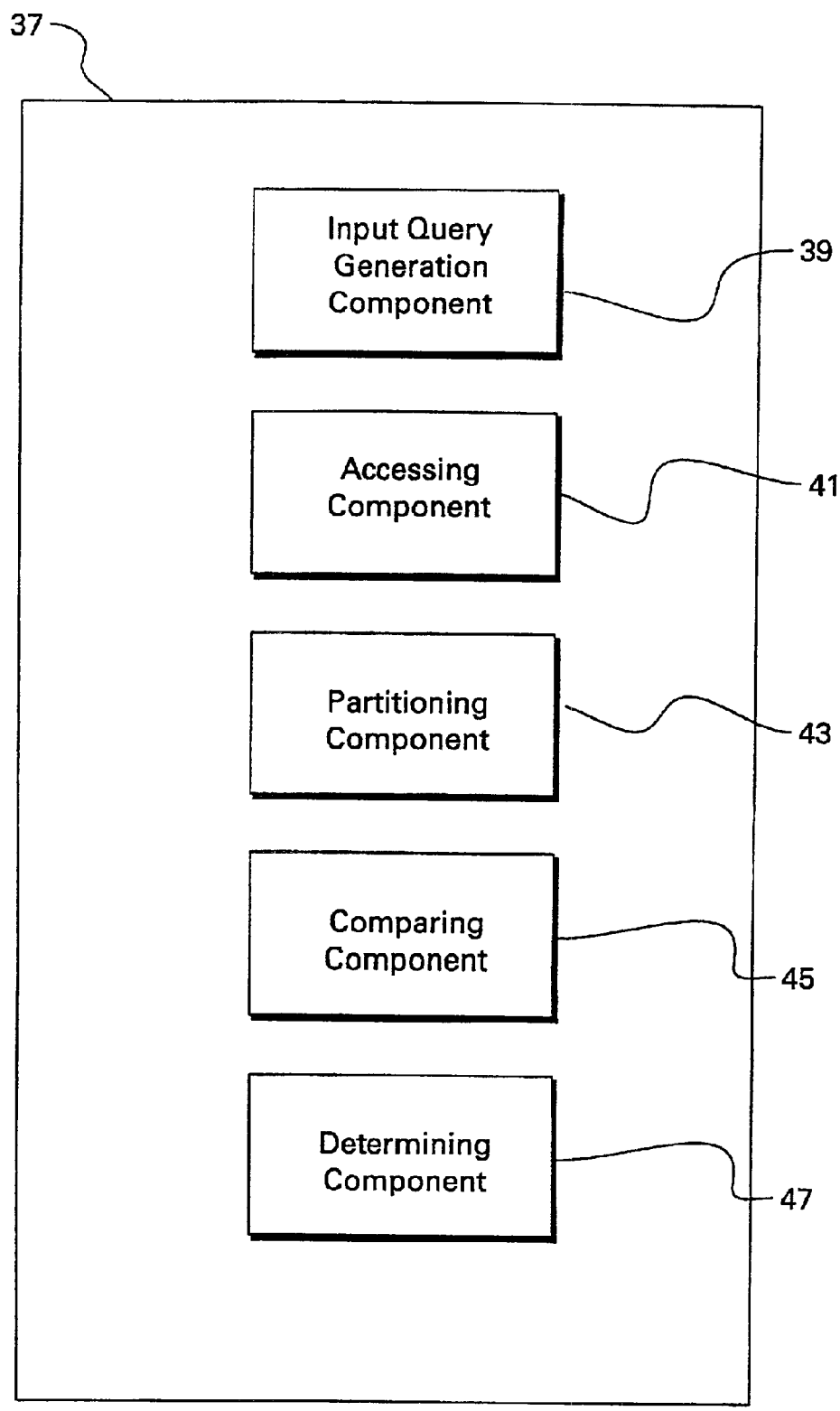
FIG. 6 shows a more detailed diagram of the domain searching component shown in FIG. 5.

FIG. 6 shows a more detailed diagram of the domain searching component 37 shown in FIG. 5. The domain searching component 37 comprises an input query generation component 39 that enables an administrator to generate an input query (e.g., (title~=*radiologist)) having a search pattern that includes a combination of attribute names, logical operators and attribute values. Generally, the input query generation component 39 generates the input query in response to the user's designation made through the computer system shown in FIG. 4. The domain searching component 37 also comprises an accessing component 41 that accesses the library of queries (e.g., (&(sn=*Neil)(title=radiologist)) et al.) used for accessing the user information in the database directory. Once the accessing component 41 has accessed the library of queries, a partitioning component 43 partitions each of the queries in the library into logical units. Each logical unit comprises a combination of an attribute name, logical operator and attribute value. For instance, using (&(sn=*Neil)(title=radiologist)) as an example of one query in the library, then (sn=*Neil) would be one logical unit and (title=radiologist) would be another logical unit. Thus, the partitioning component 43 would partition this query and all other queries in the library into their respective logical units.

A comparing component 45 compares the search pattern of the input query to each partitioned logical unit for each of the queries in the library. In particular, the comparing component 45 compares the attribute name of the input query to the attribute name in the logical unit, the operator used in the input query to the operator used in the logical unit and the attribute value in the input query to the attribute value in the logical unit. Using the above example where the input query is (title~=*radiologist) and one of the queries in the library of queries is (&(sn=*Neil)(title=radiologist)), the comparing component 45 would compare (title~= *radiologist) to each partitioned logical unit (i.e., (sn=*Neil) and (title=radiologist)). In particular, the comparing component 45 would compare the attribute name of the input query (i.e., title) to the attribute names in the logical units (i.e., sn and title). The comparing component 45 would also compare the operator used in the input query (i.e., ~=) to the operators used in the logical units (i.e., =). Also, the comparing component would compare the attribute value in the input query (i.e., *radiologist) to the attribute values in the logical units (i.e., *Neil and radiologist). Note that the comparing component 45 is able to make wildcard comparisons.

A determining component 47 determines whether there is an exact match or near match between the input query and any of the logical units associated with each of the queries in the library. In particular, the determining component 47 determines that there is an exact match if the attribute names are identical, the operator is equivalent and attribute values are equivalent. Note that the logical operators such as =, <=, >=, and ~= are considered equivalent to each other and that the logical operator != is only equivalent to itself. Using the example above, the determining component 47 would determine that there is an exact match because there is a match between all of the comparisons. More specifically, the determining component 47 would determine that there is a match between the attribute name comparison (i.e., title), operator comparison (i.e., ~= and =) and attribute value comparison (i.e., *radiologist and radiologist). Therefore, the determining component 47 would return the query as (&(sn=*Neil)(title=radiologist)) as an exact match. The comparison and match determining acts would continue for all of the other remaining queries in the library. Eventually, all of the exact matches are presented to the user.

If the determining component 47 does not find an exact match with any of the queries in the library, then the determining component will look for a near match. A near match occurs if there is a match between at least one of the attribute name comparison and operator comparison. For example, if the input query is (title~=gastroenterologist), then the determining component 47 would note that there is a near match with a query that has the pattern of (&(sn=*Neil)(title=radiologist)), because the attribute names (i.e., title) and operators (i.e., ~= and =) are identical, even though the attribute values are not. Again, the comparison and match determining acts would continue for all of the other remaining queries in the library and all of the near matches are presented to the user. If there are no near matches, then the user is notified that there are no matches, either exact or near.

The delegated administration tool 28 is not limited to a software implementation. For instance, the user group specifying component 29, domain formation component 30, administrative privileges component 32 and the information management component 36 shown in FIG. 5 may take the form of hardware or firmware or combinations of software, hardware, and firmware.

In addition, the delegated administration tool 28 is not limited to the user group specifying component 29, domain formation component 30, administrative privileges component 32 and information management component 36 including the domain searching component 37. One of ordinary skill in the art will recognize that the delegated administration tool 28 may have other components. For example, the delegated administration tool 28 could also include a workflow component that manages processes surrounding user creation and administration. Also, the delegated administration tool 28 could include a reporting component that reports usage statistics, error conditions, etc. There could also be a transactional management component that performs transactions using 2-phase commit/rollback. Still another component that the delegated administration tool 28 could include is a browsing component for viewing information associated with the hierarchy of administrative domains.

Figure 7:
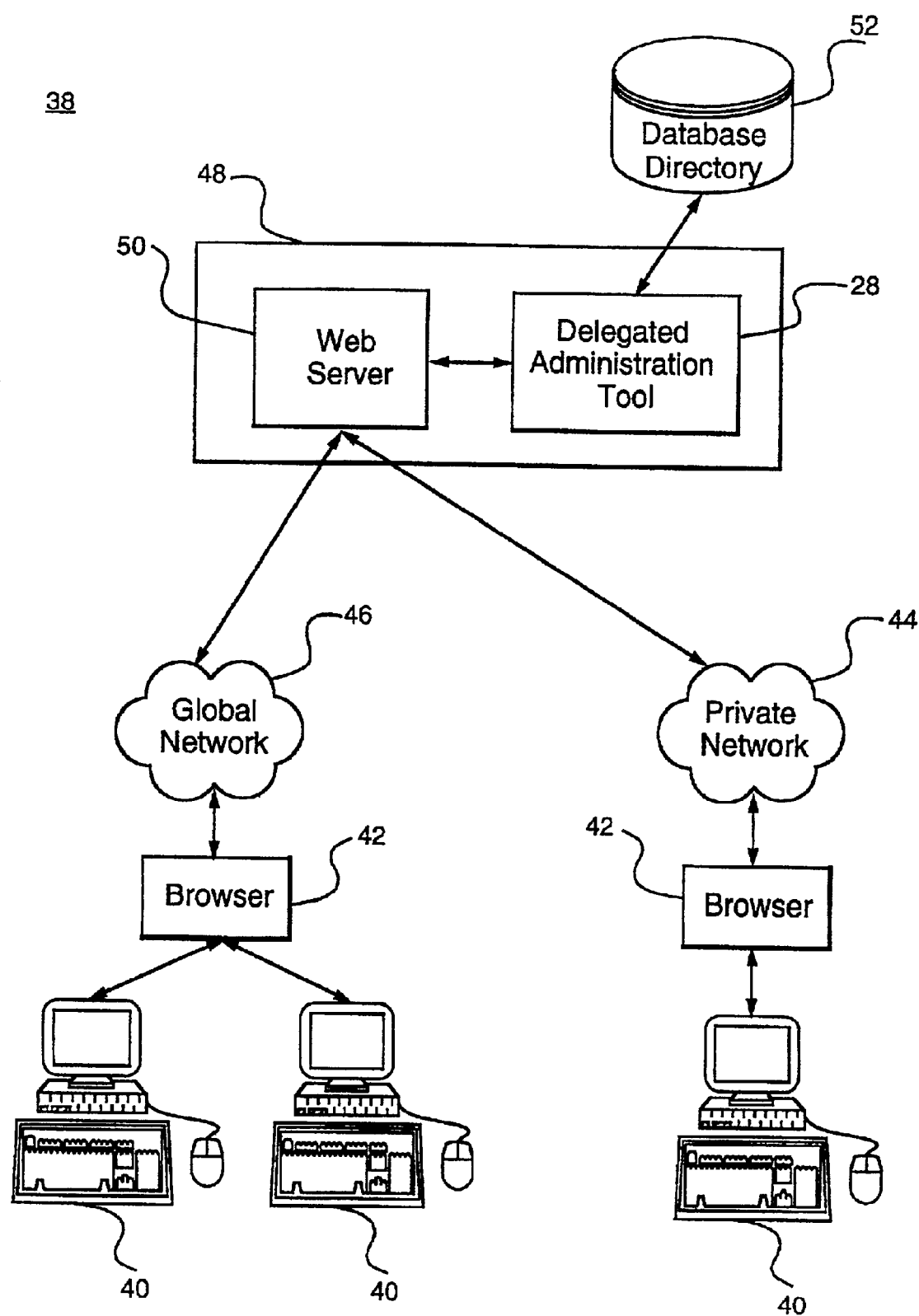
FIG. 7 shows an architectural diagram of a system for implementing the delegated administration tool that creates and administers at least one arbitrary group of users shown in FIG. 5.

FIG. 7 shows an architectural diagram of a system 38 for implementing the delegated administration tool shown in FIG. 5. FIG. 7 shows that there are several ways of accessing the delegated administration tool 28. A computing unit 40 allows an administrator to access the delegated administration tool 28. The administrator could be the SuperAdministrator or administrators with delegation authority, edit authority or other types of authority. Also, users in the domain may access the delegated administration tool 28 through a computing unit 40 to perform some basic self-administration. The computing unit 40 can take the form of a hand-held digital computer, personal digital assistant computer, notebook computer, personal computer or workstation. The administrators and users use a web browser 42 such as Microsoft INTERNET EXPLORER or Netscape NAVIGATOR to locate and display the delegated administration tool 28 on the computing unit 40. A communication network such as an electronic or wireless network connects the computing unit 40 to the delegated administration tool 28. FIG. 7 shows that the computing units 40 may connect to the delegated administration tool 28 through a private network 44 such as an extranet or intranet or a global network 46 such as a WAN (e.g., Internet). As shown in FIG. 7, the delegated administration tool 28 resides in a server 48, which comprises a web server 50 that serves the delegated administration tool 28 and a database directory 52 (or directories) that contains the various information for the users in all of the domains that form the community. However, the delegated administration tool does not have to be co-resident with the server 48. If desired, the system 38 may have functionality that enables authentication and access control of users accessing the delegated administration tool 28. Both authentication and access control can be handled at the web server level by the delegated administration tool 28 itself, or by commercially available packages such as Netegrity SITEMINDER.

The information in the database directory 52 as mentioned above may comprise information such as the user's name, location, telephone number, organization, login identification, password, etc. Other information may comprise the user's access privileges to certain resources such as applications and content. The database directory 52 may also store information on the physical devices (e.g., personal computers, servers, printers, routers, communication servers, etc.) in the networks that support the communities. Additional information stored in the database directory 52 may comprise the services (e.g., operating systems, applications, shared-file systems, print queues, etc.) Available to each of the physical devices. In addition, the database directory 52 comprises a library of queries used for accessing the user information in the directory. One of ordinary skill in the art will recognize that the library of queries does not have to be stored in the database directory 52 and instead can be stored in another similar or different type database directory or any permanent persistent storage device. The database directory 52 can take the form of a lightweight directory access protocol (LDAP) database; however, other directory type databases with other types of schema can be used with the delegated administration tool 28, including relational databases, object-oriented databases, flat files, or other data management systems.

Figure 8:
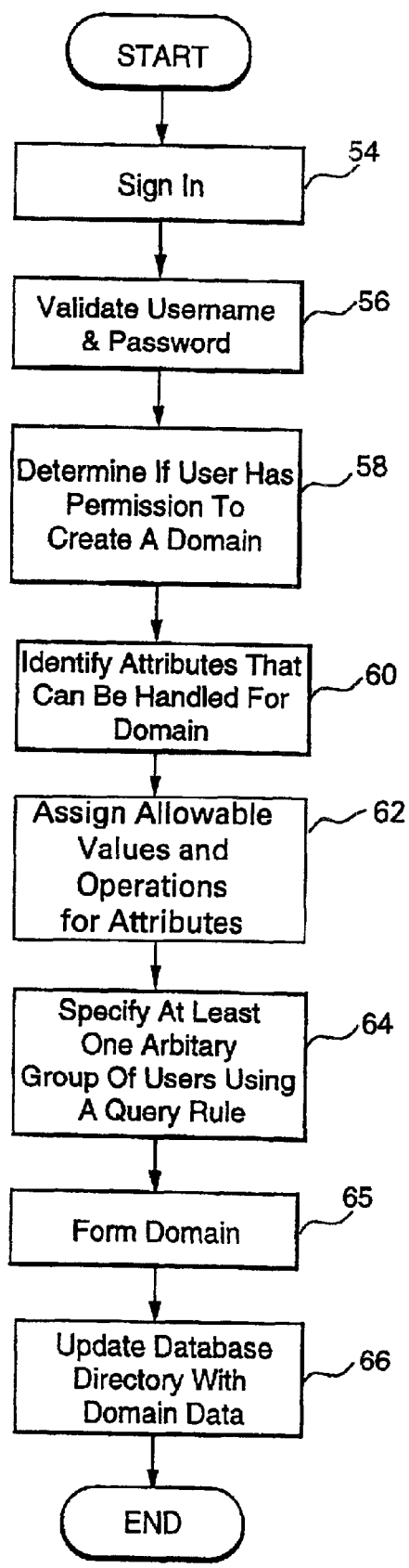
FIG. 8 shows a flow chart of the acts performed to create an administrative domain from at least one arbitrary group of users with the delegated administration tool shown in FIG. 5.

Using the system 38 shown in FIG. 7, an administrator such as a SuperAdministrator or an administrator with delegation or edit authority can use the delegated administration tool 28 to administer a community using at least one arbitrary group of users. Also, users of the community can use the delegated administration tool 28 to perform some self-administration. FIG. 8 shows a flow chart describing the acts performed to create an administrative domain from at least one arbitrary group of users with the delegated administration tool 28. To create an administrative domain, the user must be either a SuperAdministrator or an administrator having delegation authority. At block 54, the SuperAdministrator or administrator with delegation authority signs in. The sign-in act can include entering identity and security information (e.g., a valid username and password). The delegated administration tool validates the username and password at 56. The delegated administration tool then determines if the user has permission (i.e., the user is a SuperAdministrator or administrator with delegation authority) to create an administrative domain at 58. If the user is not authenticated or does not have permission to create an administrative domain, then the user is not allowed to create a domain.

At 60, the user identifies attributes that can be handled for the administrative domain. As mentioned above, attributes comprise any data, which describe information about a user (e.g., employer, job description, resources that permission has been granted to access, address, equipment used, etc.). If desired, some of the attributes can be restricted. For example, a country attribute can be restricted to a limited set of country abbreviations. For instance, in order to represent the countries United States, Canada and Mexico, a set of values can be defined such as USA, CAN or MEX, respectively. For some of these kinds of restricted attributes, it may be desirable to have the restricted attributes appear in the display to the user in the form of a pull-down menu. All of the attributes that are identified can then be viewed, edited or deleted at a subsequent time. At 62, the user assigns allowable values and operations for these identified attributes where needed.

Next, the user specifies at least one arbitrary group of users using attribute values or combinations of these values that are associated with users in a user community. In particular, the user constructs a query rule at 64 to obtain the at least one arbitrary group of users specified for the administrative domain from the database directory. The results of the query define the members of the groups of users in the community or domain. After the query rule has been constructed, the community or domain is formed at 65. Next, the database directory is updated at 66 with the data for the newly created administrative domain. If an administrator with delegation authority wants to create another domain from their operational domain, then blocks 58–66 are repeated. Otherwise, any time a SuperAdministrator or an administrator with delegation authority desires to create an administrative domain for their operational domain, then blocks 54 through 66 are repeated. Note that a SuperAdministrator for a user community can perform any function to an administrative domain that he or she desires such as create, modify, delete, view, etc.

Figure 9:
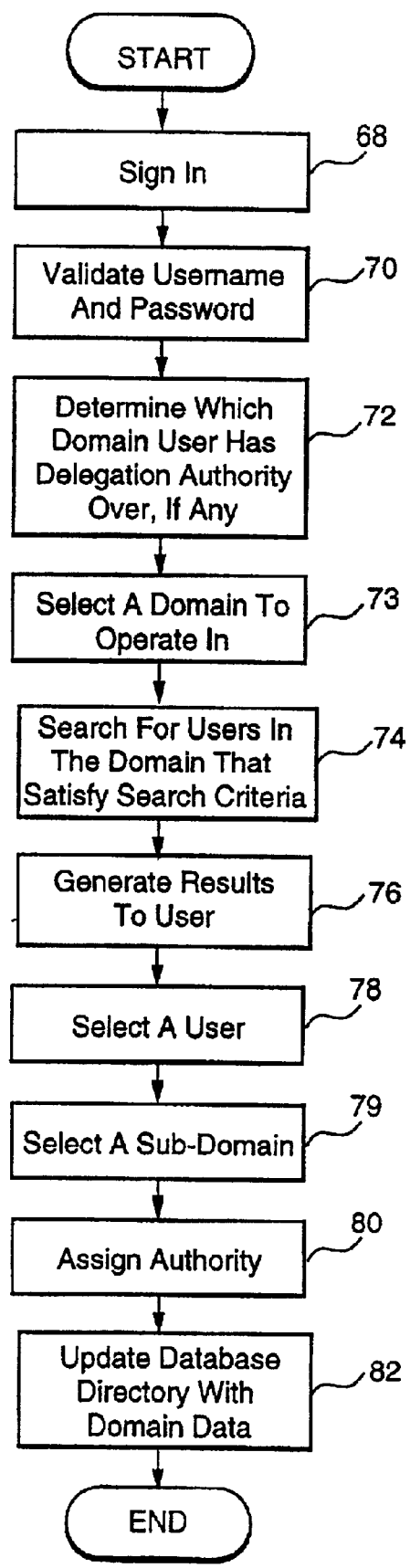
FIG. 9 shows a flow chart describing the acts performed to assign a user authority for an administrative domain formed from at least one arbitrary group of users with the delegated administration tool shown in FIG. 5.

FIG. 9 shows a flow chart describing the acts performed to assign a user delegation authority, edit authority or other types of authority for a domain. The only users that can assign delegation authority and/or edit authority are either a SuperAdministrator or an administrator having delegation authority. If the SuperAdministrator or administrator having delegation authority has not already logged onto the delegated administration tool, then he or she must sign in at 68. The delegated administration tool validates the username and password at 70. Alternatively, if the SuperAdministrator or administrator having delegation authority has already logged onto the delegated administration tool, then blocks 68–70 may be bypassed. The delegated administration tool determines which domains the user has delegation authority over, if any at 72. Thus, if the user is an administrator with delegation authority, then he or she will have permission to assign delegation authority and/or edit authority for their assigned domains.

At 73, the SuperAdministrator or administrator with delegation authority selects a particular administrative domain to operate in. The SuperAdministrator or administrator with delegation authority may select the administrative domain by inputting the desired domain or a string that describes the domain, or using a combination of both. One of ordinary skill in the art will recognize that there are other input techniques that can be used to select a domain. At 74, the SuperAdministrator or administrator with delegation authority searches for users in the database directory that satisfy search criteria that have been formulated. More detail of the processing involved with these steps is provided below. The delegated administration tool parses and formats the search results and presents the results to the user at 76. The SuperAdministrator or administrator with delegation authority then selects a single user from the results for assigning authority to that person at 78. The SuperAdministrator or administrator with delegation authority then selects a sub-domain of the active domain for which authority will be assigned to that user at 79. Then the SuperAdministrator or administrator with delegation authority selects the type of authority (i.e., delegation authority, edit authority or other types of authority) that will be assigned at 80. If desired, the SuperAdministrator or administrator with delegation authority may set an expiration date for the assigned authority. After the authority has been assigned, the database directory is updated at 82 with this data. Thus, any time an administrator with delegation authority desires to delegate authority of an assigned administrative domain to another user, then at least blocks 73 through 82 are repeated.

Figure 10:
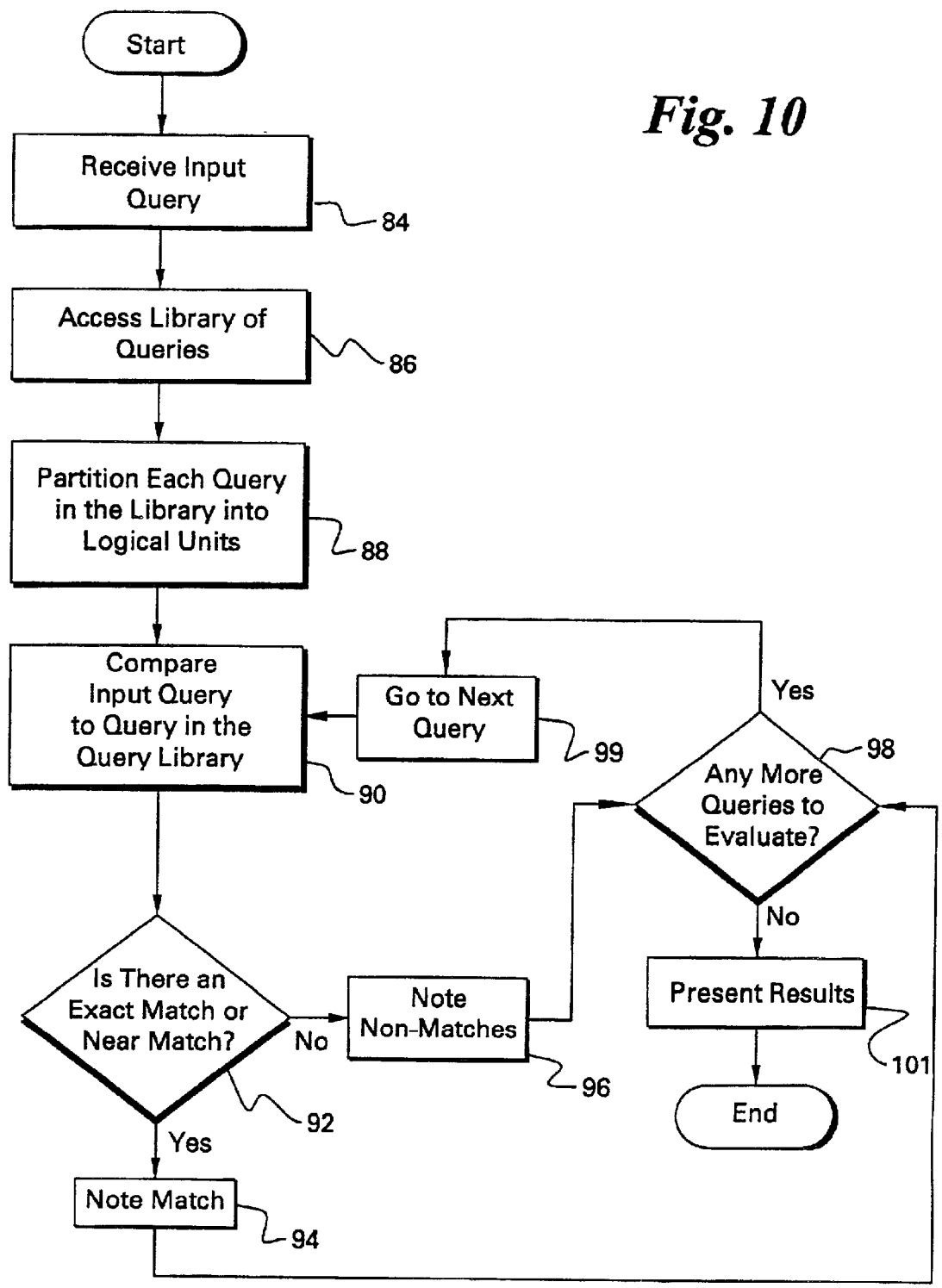
FIG. 10 shows a flow chart describing the processing acts performed in response to receiving a query for a particular domain.

FIG. 10 shows a flow chart describing the processing acts performed in response to receiving a query for a particular domain. The processing begins by receiving the input query from the user at 84. As mentioned above, the input query has a search pattern that includes a combination of attribute names, logical operators and attribute values. In response to the input query, the accessing component then accesses the library of queries used for accessing the user information in the database directory at 86. The partitioning component then partitions each of the queries in the library into logical units at 88. The comparing component then compares the input query against the first query at 90. As mentioned above, the comparing component compares the attribute name of the input query to the attribute name in the logical unit, the operator used in the input query to the operator used in the logical unit and the attribute value in the input query to the attribute value in the logical unit. The determining component then determines if there is an exact match or a near match between the input query and any of the logical units associated with each of the queries in the library at 92. As mentioned above, an exact match comprises a match with all of the comparisons, while a near match comprises a match between at least one of the comparisons. If there is either an exact match or a near match, then results are noted at 94 and non-matches are noted at 96. Next, a determination is made at 98 to determine if there are any more queries in the query library to evaluate. If there are more queries to evaluate, then the next one is obtained at 99 and then steps 90–98 are repeated until there are no more queries in the library to evaluate. Once all of the queries in the library have been compared to the input query, then a list of all matches (i.e., exact and near) are sent to the SuperAdministrator or administrator with delegation authority at 101.

Figure 11:
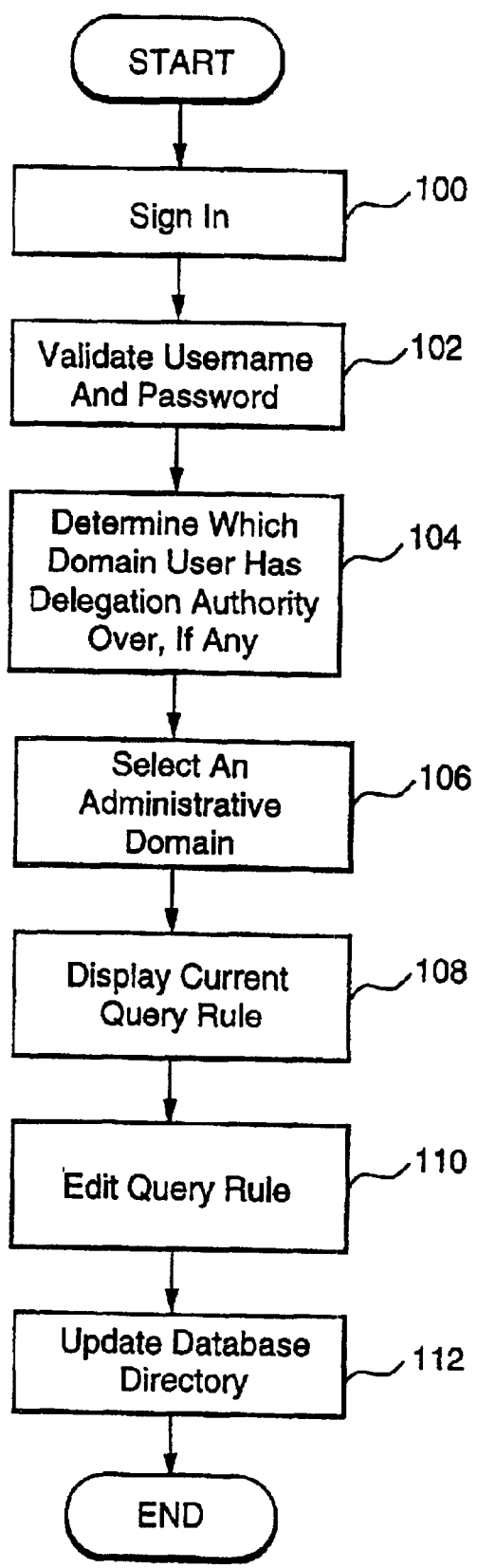
FIG. 11 shows a flow chart describing various acts performed in editing a query rule that is used to specify at least one arbitrary group of users for an administrative domain with the delegated administration tool shown in FIG. 5.

FIG. 11 shows a flow chart describing various acts performed in editing a query rule for specifying at least one arbitrary group of users for an administrative domain or sub-domain. The only users that can edit a query rule for a particular domain are a SuperAdministrator and an administrator with delegation authority in the operational domain that includes the particular domain. If the SuperAdministrator or the administrator with delegation authority has not already logged onto the delegated administration tool, then he or she must sign in at 100. The delegated administration tool validates the username and password at 102. Alternatively, if the SuperAdministrator or the administrator with delegation authority has already logged onto the delegated administration tool, then blocks 100–102 may be bypassed. The delegated administration tool then determines which domains if any that the user has delegation authority over at 104. Thus, if the user is an administrator with delegation authority then he or she will have permission to edit a query rule for any sub-domains of their assigned domains.

At 106, the SuperAdministrator or administrator with delegation authority selects a particular administrative domain that contains the query rule that he or she would like to edit and that they have authority to do so. Generally, at this block the SuperAdministrator or administrator with delegation authority inputs the domain name and/or a string that describes the domain. The delegated administration tool displays the current query rule associated with the at least one arbitrary group of users for the domain at 108. The SuperAdministrator or administrator with delegation authority then edits the query rule as desired at 110. The delegated administration tool parses and interprets the changes and updates the database directory at 112 with this data.

The foregoing flow charts of this disclosure show the functionality and operation of the delegated administration tool. In this regard, each block represents a module, segment, or portion of code, which comprises one or more executable instructions for implementing the specified logical function(s). It should also be noted that in some alternative implementations, the functions noted in the blocks may occur out of the order noted in the figures or, for example, may in fact be executed substantially concurrently or in the reverse order, depending upon the functionality involved. Also, one of ordinary skill in the art will recognize that additional blocks may be added. Furthermore, the functions can be implemented in programming languages such as C++ or JAVA; however, other languages can be used.

Figure 12A:
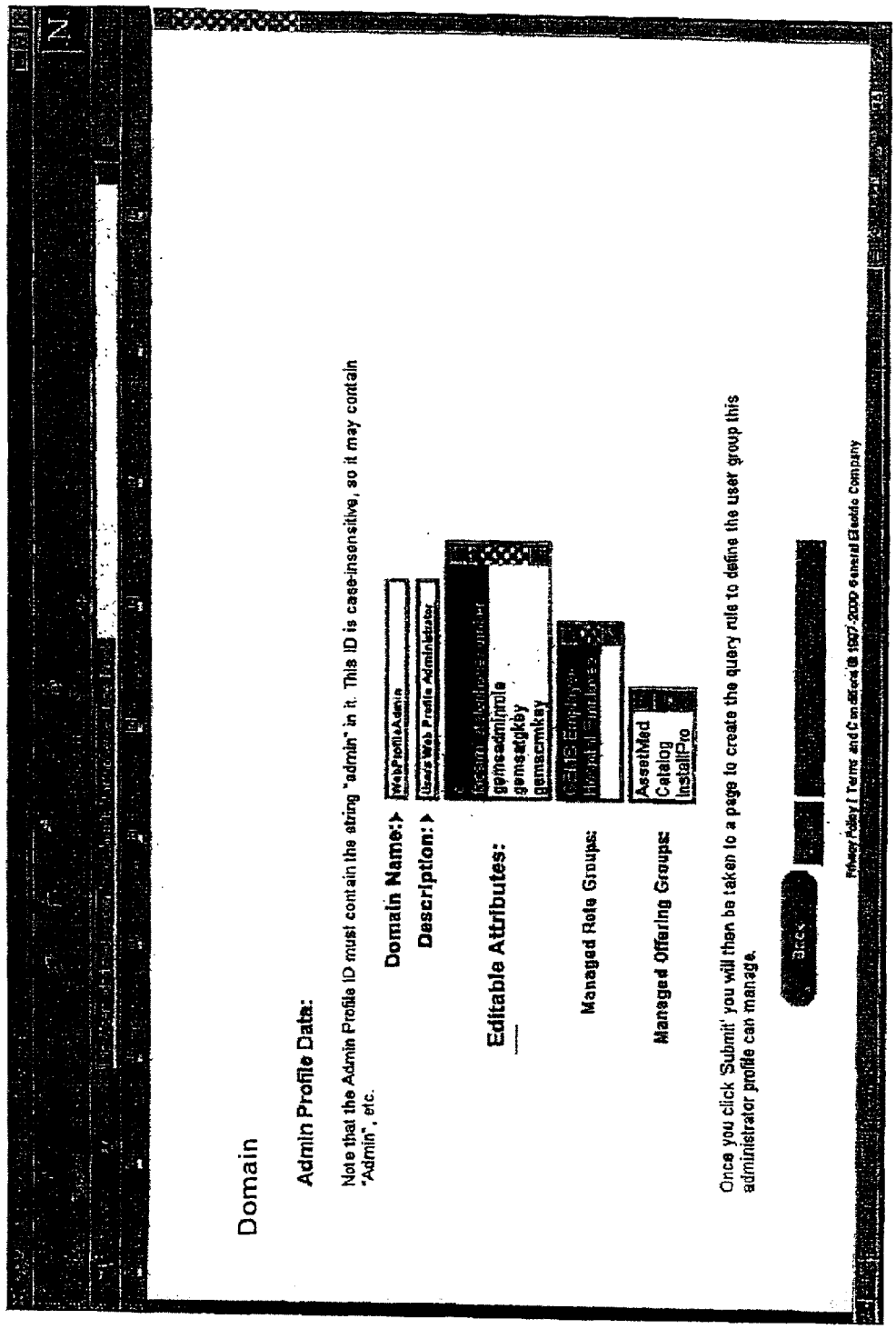
Figure 12B:
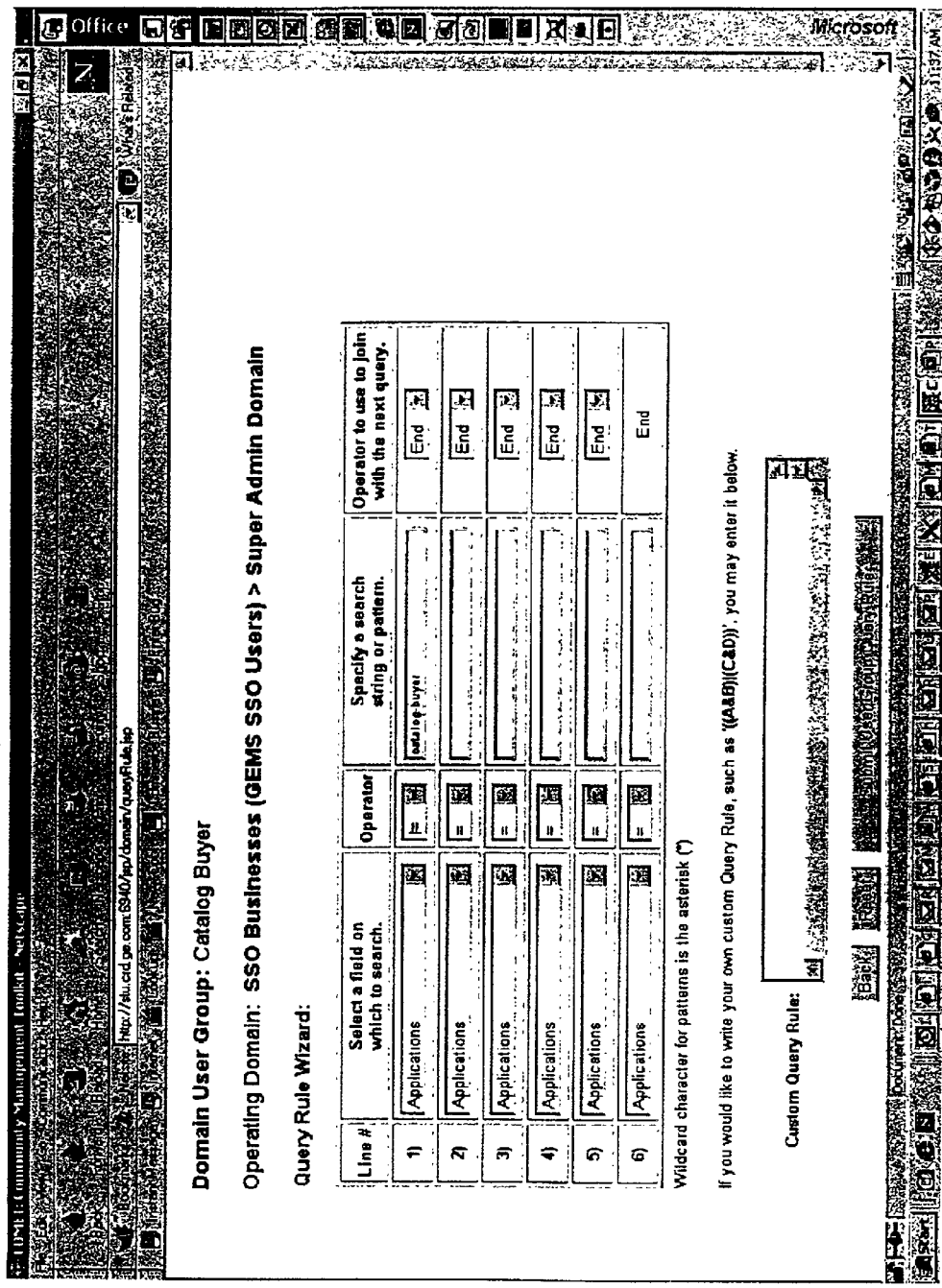

FIGS. 12*a*–12*e* show various screen displays that may be presented to a user of the delegated administration tool shown in FIG. 5. These screen displays are for illustrative purposes only and are not exhaustive of other types of displays. Also, the actual look and feel of the displays can be slightly or substantially changed during implementation. FIGS. 12*a*–12*b* show screen displays that may be presented to a user after he or she logs into the delegated administration tool 28 and is interested in adding an administrative domain from at least one arbitrary group of users. In particular, FIG. 12*a* shows a screen display that enables a user to create or edit an administrative domain from at least one arbitrary group of users. In FIG. 12*a*, the user identifies the administrative domain name and attributes that can be handled for the domain. FIG. 12*b* shows a screen display that enables a user to construct or edit a query rule for specifying the at least one arbitrary group of users for forming an administrative domain or sub-domain. Each query rule logical unit on a line comprises an attribute field for searching, an operator such as "equal to", "less than", "greater than", "less than or equal to", "greater than or equal to", "not equal to", "contains", "does not contain", "excludes", or "does not exclude"; a field for specifying a string or pattern for searching the designated attribute; and another operator such as "AND", or "OR" for coupling this particular query rule to any other rules. One of ordinary skill in the art will recognize that other fields and additional attribute operators can be used to construct a query rule. The screen display in FIG. 12*b* also presents the user with the option of constructing his or her own custom-made query rule. Constructing a custom-made query rule can be achieved by using Boolean logic, a natural language query or an SQL query.

Figure 12C:
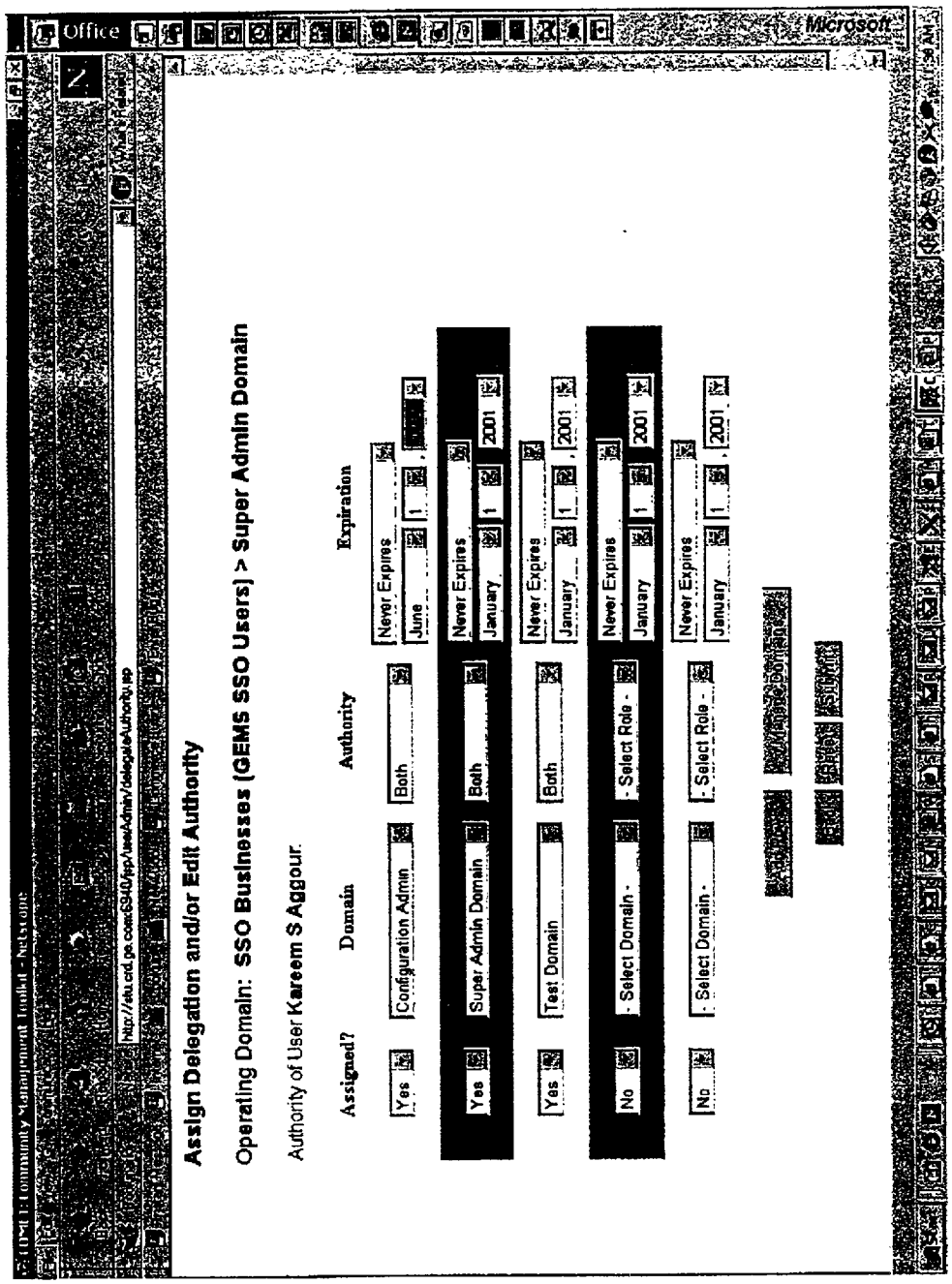

FIG. 12*c* shows a screen display that may be presented to a user after he or she logs into the delegated administration tool 28 and is interested in assigning delegation authority, edit authority or any other type of authority. In FIG. 12*c*, the user has selected a particular user for delegating administration and identifies the administrative domain name and the type of authority (e.g., delegation authority and/or edit authority) that the user will have over that domain. In addition, an expiration date for the assigned administrative domain and authority can be designated. Note that more than one administrative domain can be assigned to a user. Similarly, more than one user may be assigned to a domain. The selections for the domain name, the type of authority and expiration date appear in FIG. 12*c* as pull-down menus; however, other options for inputting data may be used if desired.

FIGS. 12*d*–12*e* show screen displays that may be presented to a user that is interested in searching for an administrative domain for a selected community. In particular, FIG. 12*d* shows a screen display that enables a user to specify a search criterion for a particular administrative domain, while FIG. 12*e* displays the list of domains and their query rules that matched the search criterion. In addition, the display in FIG. 12*e* shows that user has the option to enter another domain search criterion.

The above-described delegated administration tool comprises an ordered listing of executable instructions for implementing logical functions. The ordered listing can be embodied in any computer-readable medium for use by or in connection with a computer-based system that can retrieve the instructions and execute them. In the context of this application, the computer-readable medium can be any means that can contain, store, communicate, propagate, transmit or transport the instructions. The computer readable medium can be an electronic, a magnetic, an optical, an electromagnetic, or an infrared system, apparatus, or device. An illustrative, but non-exhaustive list of computer-readable mediums can include an electrical connection (electronic) having one or more wires, a portable computer diskette (magnetic), a random access memory (RAM) (magnetic), a read-only memory (ROM) (magnetic), an erasable programmable read-only memory (EPROM or Flash memory) (magnetic), an optical fiber (optical), and a portable compact disc read-only memory (CDROM) (optical).

Note that the computer readable medium may comprise paper or another suitable medium upon which the instructions are printed. For instance, the instructions can be electronically captured via optical scanning of the paper or other medium, then compiled, interpreted or otherwise processed in a suitable manner if necessary, and then stored in a computer memory.

It is apparent that there has been provided in accordance with this invention, a delegated administration tool. While the invention has been particularly shown and described in conjunction with a preferred embodiment thereof, it will be appreciated that variations and modifications can be effected by a person of ordinary skill in the art without departing from the scope of the invention.

What is claimed is:

1. A method for matching an input query having a search pattern that includes a combination of attribute names, logical operators and attribute values to a library of queries used for accessing information in a database directory, comprising:

partitioning each of the queries in the library into logical units, wherein each logical unit comprises a combination of an attribute name, logical operator and attribute value;

for each of the queries in the library, comparing the search pattern of the input query to each partitioned logical unit, wherein the comparing comprises comparing the attribute name of the input query to the attribute name in the logical unit, the operator used in the input query to the operator used in the logical unit and the attribute value in the input query to the attribute value in the logical unit; and determining whether there is a match between the input query and any of the logical units associated with each of the queries in the library, wherein the determining of a match comprises finding a near match.

2. The method according to claim 1, wherein the determining of a near match comprises deciding whether there is a match between at least one of the comparisons between the attribute name of the input query and the attribute name in the logical unit and the operator used in the input query and the operator used in the logical unit.

3. The method according to claim 1, wherein the determining of a match further comprises finding an exact match.

4. The method according to claim 3, wherein the determining of an exact match comprises deciding whether there is a match between the comparisons of the attribute name of the input query and the attribute name in the logical unit, the operator used in the input query and the operator used in the logical unit and the attribute value in the input query and the attribute value in the logical unit.

5. A method for matching an input query having a search pattern that includes a combination of attribute names, logical operators and attribute values to a library of queries used for accessing information in a database directory, comprising:

partitioning each of the queries in the library into logical units, wherein each logical unit comprises a combination of an attribute name, logical operator and attribute value;

for each of the queries in the library, comparing the search pattern of the input query to each partitioned logical unit, wherein the comparing comprises comparing the attribute name of the input query to the attribute name in the logical unit, the operator used in the input query to the operator used in the logical unit and the attribute value in the input query to the attribute value in the logical unit; and determining whether there is a match between the input query and any of the logical units associated with each of the queries in the library, wherein a match comprises an exact match and a near match.

6. A method for querying a database directory containing user information associated with a user community, comprising:

generating an input query having a search pattern that includes a combination of attribute names, logical operators and attribute values;

accessing a library of queries used for accessing the user information in the database directory;

partitioning each of the queries in the library into logical units, wherein each logical unit comprises a combination of an attribute name, logical operator and attribute value;

for each of the queries in the library, comparing the search pattern of the input query to each partitioned logical unit, wherein the comparing comprises comparing the attribute name of the input query to the attribute name in the logical unit, the operator used in the input query to the operator used in the logical unit and the attribute value in the input query to the attribute value in the logical unit; and determining whether there is a match between the input query and any of the logical units associated with each of the queries in the library, wherein the determining of a match comprises finding a near match.

7. The method according to claim 6, wherein the determining of a near match comprises deciding whether there is a match between at least one of the comparisons between the attribute name of the input query and the attribute name in the logical unit and the operator used in the input query and the operator used in the logical unit.

8. The method according to claim 6, herein the determining of a match further comprises finding an exact match.

9. The method according to claim 8, wherein the determining of an exact match comprises deciding whether there is a match between the comparisons of the attribute name of the input query and the attribute name in the logical unit, the operator used in the input query and the operator used in the logical unit and the attribute value in the input query and the attribute value in the logical unit.

10. A method for enabling an administrator to query a database directory containing user information associated with a user community, comprising:

prompting the administrator to generate an input query having a search pattern that includes a combination of attribute names, logical operators and attribute values;

accessing a library of queries used for accessing the user information in the database directory in response to the input query generated by the administrator;

partitioning each of the queries in the library into logical units, wherein each logical unit comprises a combination of an attribute name, logical operator and attribute value;

for each of the queries in the library, comparing the search pattern of the input query to each partitioned logical unit, wherein the comparing comprises comparing the attribute name of the input query to the attribute name in the logical unit, the operator used in the input query to the operator used in the logical unit and the attribute value in the input query to the attribute value in the logical unit;

determining whether there is a match between the input query and any of the logical units associated with each of the queries in the library, wherein the determining of a match comprises finding a near match that comprises a match between at least one of the comparisons between the attribute name of the input query and the attribute name in the logical unit and the operator used in the input query and the operator used in the logical unit; and informing the administrator of whether there is a match with the input query.

11. The method according to claim 10, wherein the determining of a match further comprises finding an exact match that comprises a match between the comparisons of the attribute name of the input query and the attribute name in the logical unit, the operator used in the input query and the operator used in the logical unit and the attribute value in the input query and the attribute value in the logical unit.

12. A tool for matching an input query having a search pattern that includes a combination of attribute names, logical operators and attribute values to a library of queries used for accessing information in a database directory, comprising:

means for partitioning each of the queries in the library into logical units, wherein each logical unit comprises a combination of an attribute name, logical operator and attribute value;

means for comparing the search pattern of the input query to each partitioned logical unit for each of the queries in the library, wherein the comparing means compares the attribute name of the input query to the attribute name in the logical unit, the operator used in the input query to the operator used in the logical unit and the attribute value in the input query to the attribute value in the logical unit; and means for determining whether there is a match between the input query and any of the logical units associated with each of the queries in the library, wherein the determining means finds a near match that comprises a match between at least one of the comparisons between the attribute name of the input query and the attribute name in the logical unit and the operator used in the input query and the operator used in the logical unit.

13. The tool according to claim 12, wherein the determining means further finds an exact match that comprises a match between the comparisons of the attribute name of the input query and the attribute name in the logical unit, the operator used in the input query and the operator used in the logical unit and the attribute value in the input query and the attribute value in the logical unit.

14. A user community administration tool for querying a database directory containing user information associated with a user community, comprising:

an input query generation component that generates an input query having a search pattern that includes a combination of attribute names, logical operators and attribute values;

an accessing component that accesses a library of queries used for accessing the user information in the database directory;

a partitioning component that partitions each of the queries in the library into logical units, wherein each logical unit comprises a combination of an attribute name, logical operator and attribute value;

a comparing component that compares the search pattern of the input query to each partitioned logical unit for each of the queries in the library, wherein the comparing component compares the attribute name of the input query to the attribute name in the logical unit, the operator used in the input query to the operator used in the logical unit and the attribute value in the input query to the attribute value in the logical unit; and a determining component that determines whether there is a match between the input query and any of the logical units associated with each of the queries in the library, wherein the determining component finds a near match that comprises a match between at least one of the comparisons between the attribute name of the input query and the attribute name in the logical unit and the operator used in the input query and the operator used in the logical unit.

15. The tool according to claim 14, wherein the determining component further finds an exact match that comprises a match between the comparisons of the attribute name of the input query and the attribute name in the logical unit, the operator used in the input query and the operator used in the logical unit and the attribute value in the input query and the attribute value in the logical unit.

16. A system for querying user information associated with a user community, comprising:

a database directory containing a plurality of user information;

a user community administration tool to query the database directory comprising an input query generation component that generates an input query having a search pattern that includes a combination of attribute names, logical operators and attribute values; an accessing component that accesses a library of queries used for accessing the user information in the database directory; a partitioning component that partitions each of the queries in the library into logical units, wherein each logical unit comprises a combination of an attribute name, logical operator and attribute value; a comparing component that compares the search pattern of the input query to each partitioned logical unit for each of the queries in the library, wherein the comparing component compares the attribute name of the input query to the attribute name in the logical unit, the operator used in the input query to the operator used in the logical unit and the attribute value in the input query to the attribute value in the logical unit; and a determining component that determines whether there is a match between the input query and any of the logical units associated with each of the queries in the library, wherein the determining component finds a near match that comprises a match between at least one of the comparisons between the attribute name of the input query and the attribute name in the logical unit and the operator used in the input query and the operator used in the logical unit; and a first computing unit configured to serve the user community administration tool and the database directory.

17. The system according to claim 16, further comprising a second computing unit configured to execute the user community administration tool served from the first computing unit over a network.

18. The system according to claim 16, wherein the determining component further finds an exact match that comprises a match between the comparisons of the attribute name of the input query and the attribute name in the logical unit, the operator used in the input query and the operator used in the logical unit and the attribute value in the input query and the attribute value in the logical unit.

19. A computer-readable medium storing computer instructions for instructing a computer system to match an input query having a search pattern that includes a combination of attribute names, logical operators and attribute values to a library of queries used for accessing information in a database directory, the computer instructions comprising:

partitioning each of the queries in the library into logical units, wherein each logical unit comprises a combination of an attribute name, logical operator and attribute value;

for each of the queries in the library, comparing the search pattern of the input query to each partitioned logical unit, wherein the comparing comprises comparing the attribute name of the input query to the attribute name in the logical unit, the operator used in the input query to the operator used in the logical unit and the attribute value in the input query to the attribute value in the logical unit; and determining whether there is a match between the input query and any of the logical units associated with each of the queries in the library, wherein the determining of a match comprises instructions for finding a near match.

20. The computer-readable medium according to claim 19, wherein the determining of a near match comprises instructions for deciding whether there is a match between at least one of the comparisons between the attribute name of the input query and the attribute name in the logical unit and the operator used in the input query and the operator used in the logical unit.

21. The computer-readable medium according to claim 19, wherein the determining of a match further comprises instructions for finding an exact match.

22. The computer-readable medium according to claim 21, wherein the determining of an exact match comprises instructions for deciding whether there is a match between the comparisons of the attribute name of the input query and the attribute name in the logical unit, the operator used in the input query and the operator used in the logical unit and the attribute value in the input query and the attribute value in the logical unit.

23. A computer-readable medium storing computer instructions for instructing a computer system to match an input query having a search pattern that includes a combination of attribute names, logical operators and attribute values to a library of queries used for accessing information in a database directory, the computer instructions comprising:

partitioning each of the queries in the library into logical units, wherein each logical unit comprises a combination of an attribute name, logical operator and attribute value;

for each of the queries in the library, comparing the search pattern of the input query to each partitioned logical unit, wherein the comparing comprises comparing the attribute name of the input query to the attribute name in the logical unit, the operator used in the input query to the operator used in the logical unit and the attribute value in the input query to the attribute value in the logical unit; and determining whether there is a match between the input query and any of the logical units associated with each of the queries in the library, wherein a match comprises an exact match and a near match.

24. A computer-readable medium storing computer instructions for instructing a computer system to query a database directory containing user information associated with a user community, the computer instructions comprising:

generating an, input query having a search pattern that includes a combination of attribute names, logical operators and attribute values;

accessing a library of queries used for accessing the user information in the database directory;

partitioning each of the queries in the library into logical units, wherein each logical unit comprises a combination of an attribute name, logical operator and attribute value;

for each of the queries in the library, comparing the search pattern of the input query to each partitioned logical unit, wherein the comparing comprises comparing the attribute name of the input query to the attribute name in the logical unit, the operator used in the input query to the operator used in the logical unit and the attribute value in the input query to the attribute value in the logical unit; and determining whether there is a match between the input query and any of the logical units associated with each of the queries in the library, wherein the determining of a match comprises instructions for finding a near match.

25. The computer-readable medium according to claim 24, wherein the determining of a near match comprises instructions for deciding whether there is a match between at least one of the comparisons between the attribute name of the input query and the attribute name in the logical unit and the operator used in the input query and the operator used in the logical unit.

26. The computer-readable medium according to claim 24, wherein the determining of a match further comprises instructions for finding an exact match.

27. The computer-readable medium according to claim 26, wherein the determining of an exact match comprises instructions for deciding whether there is a match between the comparisons of the attribute name of the input query and the attribute name in the logical unit, the operator used in the input query and the operator used in the logical unit and the attribute value in the input query and the attribute value in the logical unit.

28. A computer-readable medium storing computer instructions for instructing a computer system to enable an administrator to query a database directory containing user information associated with a user community, the computer instructions comprising:

prompting the administrator to generate an input query having a search pattern that includes a combination of attribute names, logical operators and attribute values;

accessing a library of queries used for accessing the user information in the database directory in response to the input query generated by the administrator;

partitioning each of the queries in the library into logical units, wherein each logical unit comprises a combination of an attribute name, logical operator and attribute value;

for each of the queries in the library, comparing the search pattern of the input query to each partitioned logical unit, wherein the comparing comprises comparing the attribute name of the input query to the attribute name in the logical unit, the operator used in the input query to the operator used in the logical unit and the attribute value in the input query to the attribute value in the logical unit;

determining whether there is a match between the input query and any of the logical units associated with each of the queries in the library, wherein the determining of a match comprises instructions for finding a near match that comprises a match between at least one of the comparisons between the attribute name of the input query and the attribute name in the logical unit and the operator used in the input query and the operator used in the logical unit; and informing the administrator of whether there is a match with the input query.

29. The computer-readable medium according to claim 28, wherein the determining of a match further comprises instructions for finding an exact match that comprises a match between the comparisons of the attribute name of the input query and the attribute name in the logical unit, the operator used in the input query and the operator used in the logical unit and the attribute value in the input query and the attribute value in the logical unit.

* * * * *